United States Patent [19]
Mayevsky

[11] Patent Number: 5,685,313
[45] Date of Patent: Nov. 11, 1997

[54] TISSUE MONITOR

[75] Inventor: Avraham Mayevsky, Ramat Gan, Israel

[73] Assignee: Brain Monitor Ltd., Ramat Gan, Israel

[21] Appl. No.: 251,765

[22] Filed: May 31, 1994

[51] Int. Cl.[6] .......................................... A61B 6/00
[52] U.S. Cl. .................................... 128/665; 128/633
[58] Field of Search .......................... 128/633, 634, 128/635, 665, 666, 667, 672, 673, 675, 692, 736

[56] References Cited

U.S. PATENT DOCUMENTS

| | | | |
|---|---|---|---|
| 4,830,849 | 5/1989 | Osterholm | 128/632 |
| 4,945,896 | 8/1990 | Gade | 128/691 |
| 4,966,148 | 10/1990 | Millar | 128/673 |
| 4,981,138 | 1/1991 | Deckelbaum et al. | 128/665 |
| 4,986,671 | 1/1991 | Sun et al. | 128/692 |
| 5,166,990 | 11/1992 | Riccitelli | 128/692 |
| 5,187,672 | 2/1993 | Chance et al. | 128/633 |
| 5,207,227 | 5/1993 | Powers | 128/736 |
| 5,305,745 | 4/1994 | Zacouto | 128/633 |
| 5,382,163 | 1/1995 | Putnam | 128/665 |
| 5,419,312 | 5/1995 | Arenberg et al. | 128/736 |
| 5,439,000 | 8/1995 | Gunderson et al. | 128/664 |
| 5,582,168 | 12/1996 | Samuels et al. | 128/633 |

OTHER PUBLICATIONS

Mayevsky, Brain NADH Redox State Monitored In Vivo by Fiber Optic Surface Fluorometry, Brain Research Reviews, 7 (1984) 49–68.

*Primary Examiner*—Brian L. Casler
*Attorney, Agent, or Firm*—Mark M. Friedman

[57] ABSTRACT

A single signal-single probe multiparameter analyzer apparatus for monitoring various parameters of the identical volume element of body tissue, which includes an input signal generator, a single signal guide which transmits input signal in, and transmits output signal out, constituting a single signal-single probe, a signal splitter which splits output signal into two or more parts, filters which separate various components of output signal, detectors which measure the different components of the output signal, a computer and an analog to digital convertor; and algorithms to evaluate the data.

5 Claims, 15 Drawing Sheets

TISSUE MONITOR

FIELD AND BACKGROUND OF THE INVENTION

Mammalian tissues are dependent upon the continuous supply of metabolic energy (such as ATP and phosphocreatine) in order to perform its various vital activities (biosynthesis, ion transport, etc.). The main source of energy to be utilized by most body tissues is glucose transported by the blood stream together with oxygen (FIG. 1A). The oxygen and glucose pass from the vascular compartment to the cells through the extracellular space. The $O_2$ molecule serves as a terminal electron acceptor in the respiratory chain located in the inner membrane of the mitochondrion. Under normal $O_2$ supply, the complicated enzymatic processes of glucose breakdown to $CO_2$ and $H_2O$ could be divided into two major steps, namely, the anaerobic (not dependent on $O_2$), followed by the aerobic step ($O_2$ dependent) which occurs in the mitochondrion. See FIG. 1B. Changes in tissue energy metabolism may have a transient nature or may be permanent. Therefore, in order to assess the tissue energy state, it is necessary to monitor the events continuously in real-time mode.

Any change in brain electrical activity will result in an activation of the ion pumps in an effort to restore normal ion distribution. A decrease (ischemia) or increase (hyperoxia) in the $O_2$ supply to the brain will affect the balance between energy supply and demand and may result in a pathological state. In the pioneering work described by Chance and Williams (Chance B. and Williams, G. R., "Respiratory enzymes in oxidative phosphorylation. I- Kinetics of oxygen utilization", J. Biol. Chem. 217, 383–393, 1955), which is incorporated by reference as if fully set forth herein, several metabolic states for the isolated mitochondria depending upon the availability of $O_2$, substrate and ADP, were defined. The "resting state", state 4, exhibited high $O_2$ and substrate levels, with the limiting factor being the ADP. The active state, state 3, could be induced by the addition of ADP to the resting mitochondria. This will lead to the formation of more ATP and to the oxidation of the various electron carriers in the mitochondria. In state 3, which is the active state during which $O_2$ consumption is increased, cerebral blood flow will increase in order to compensate for the increased $O_2$ consumption (Mayevsky, A. and Weiss, H. R., Cerebral blood flow and oxygen consumption in cortical spreading depression, J. CBF and Metabol. 11:829–836 (1991), which is incorporated by reference as if fully set forth herein). While in state 4, 99% of the Nicotine Adeninc Dinucleotide (NADH) will be in the reduced form, in state 3 only about 50% of the NADH will be oxidized. The "resting" brain in vivo is probably between state 4 and state 3 (Mayevsky, A., Brain energy metabolism of the conscious rat exposed to various physiological and pathological situations, Brain Res. 113:327–338 (1976), which is incorporated by reference as if fully set forth herein).

There is a direct coupling between energy metabolism of the cellular compartment and the blood flow in the microcirculation of the same tissue. In a normal tissue any change in $O_2$ supply (decrease or increase) will be compensated by a change in blood flow (increase or decrease, respectively). By this mechanism, $O_2$ supply will remain constant if $O_2$ consumption was not affected. In cases when $O_2$ consumption is stimulated by activation of ion pumping activity or biosynthesis, the blood flow will be stimulated in order to supply more $O_2$. See FIG. 1B.

A change in blood flow and volume (i.e., in intra vascular velocity and concentration of red blood corpuscles) may change the apparent energy state. See FIG. 1A. Knowledge of the blood supply via microcirculatory blood flow (MBF) by itself or of the mitochondrial redox state of Nicotine Adeninc Dinucleotide (NADH), by itself, is of limited value. It will not provide reliable information due to various unclear responses to pathological events such as hypoxia, ischemia or brain stimulation (epileptic activity or spreading depression).

The effects of ischemia on the CBF of the brain were tested in the Mongolian gerbil in which partial or complete ischemia can be induced by unilateral or bilateral carotid artery occlusions (Mayevsky, A. Level of ischemia and brain functions in the Mongolian gerbil in vivo, Brain Res., 524:1–9 (1990), which is incorporated by reference as if fully set forth herein). 38 occlusions (unilateral or bilateral) were performed in a group of 28 gerbils. The level of ischemia as evaluated by the Laser Doppler flowmeter was compared to the intramitochondrial change in the NADH redox state. The two parameters were normalized to the rage of 0 to 100% and the results, which are presented in FIG. 1D, show a significant correlation between the decrease in flow (increase ischemia) and the increase in NADH levels ($R=0.73$, $p<0.001$, $N=38$). Note the significant scatter in the data which demonstrates another shortcoming of using two separate instruments.

The use of these two parameters enables one to quantify the level of ischemia and tissue $O_2$ deficiency and overcomes the inability to quantify those two parameters in absolute units (such as ml CBF per unit time). In order to reliably assess tissue energy state, it is necessary to monitor both MBF and NADH continuously from the same volume element of tissue.

The present invention relates to an apparatus for monitoring the viability of body tissue. In particular, the present invention relates to an apparatus or device for measuring two or more parameters indicative of the function of the tissue, storing and retrieving said information, enabling long term monitoring.

More particularly, the present invention relates to a single probe device that measures parameters indicative of the function of the tissue in the identical volume element of the tissue (determining their unique ratios) storing and retrieving said information, to enable long term monitoring.

Most particularly, the main two parameters to be monitored from the tissue are microcirculatory blood flow (MBF) and mitochondrial redox state (NADH fluorescence), as these provide considerable tissue viability information. Until now MBF was measured by Laser Doppler flowmetry while mitochondrial redox state was evaluated by monitoring oxidation reduction state of NADH (Mayevsky, A., Brain NADH redox state monitored in vivo by fiber optic surface fluorometry, Brain Res. Rev. 7: 49–68, (1984), which is incorporated by reference as if fully set forth herein). These measurements were done by using two separate instruments utilizing specific optical properties of the red blood cells and the mitochondrial enzymatic activities. In the present application it is suggested to monitor tissue blood flow (MBF) and intramitochondrial redox state (NADH) of the same volume element of tissue, at the same time, using a single probe, with two or more analyzers of the return signals.

The prior art teaches a wide variety of apparatus/devices which monitor various parameters reflecting the viability of the tissue. For example, U.S. Pat. No. 4,703,758 teaches the use of an apparatus to monitor blood flow by using a light source to emit a beam of light and a light detector that measures the light received. This provides the value of the intensity of the transmitted light, which inter alia depends upon the blood flow in the path of the light.

U.S. Pat. No. 4,945,896 teaches the use of a multiprobe sensor, using independent microelectrodes implanted inside the brain tissue, for measuring various parameters indicative of the function of the brain including a laser doppler flow probe for measuring cerebral blood flow, and a probe for monitoring redox state (NADH). These probes can be put in sequentially, i.e., one after another in the same housing, or they both can be in together, side by side.

These devices suffer from a major drawback. Tissue viability is not merely a reflection of various values of parameters measured at different times in one place, or different places at one time. Rather, the values of blood flow and redox state (NADH) must be monitored simultaneously on the identical volume element of tissue. The complex biochemical mechanisms that determine tissue viability are such that short time deviations between measurement or short distances between points of measurement can provide inaccurate or even misleading information. For example, illuminating an organ in the UV (366 nm) causes fluorescence (at 440 to 480 nm). The measured intensity of this fluorescence reflects the oxidation-reduction state ((NADH) /(NAD ratio) of this organ. However, variation in intra-tissue concentration of red blood corpuscles effects the measurement.

In particular, a reduction of these red blood corpuscles causes an increase in fluorescence, generating a false indication of the true oxidation reduction state of the organ. Hence, U.S. Pat. No. 4,449,535 teaches the use of simultaneously monitoring the concentration of red corpuscles, by illuminating at a red wavelength (720 nm) at the same time, at the same spot or place as the UV, and measuring the variation in intensity of the reflected red radiation as well as the fluorescence at 440–480 nm, the former being representative of the intra-tissue concentration of red blood corpuscles.

This approach involves concentrating both the UV and red pulses onto a single point, an optical fiber to convey both pulses in one direction, and fluorescence and reflected radiation in the other, and two photoelectric receivers for detecting the respective wavelengths. The quality of the information is limited both by the possibility that the red radiation is a perturbation to the tissue that can affect its fluorescence (and vice versa) and by the need to prevent interference between the two output signals (e.g., interference reflections being picked up by the receivers). The use of red radiation to correct for blood hemodynamic artifacts in the NADH signal introduces inaccuracies into the measurements due to differences in absorption volume.

Furthermore, because the different radiations penetrate the tissue to different extents, effectively two different elements of tissue volume are being probed, even if both radiations fall on same spot or place. Also, as two different wavelengths and two different sources of radiation are used, there is a relative instability associated with the reflectometer and fluorimeter readings, especially with time sharing compared to using a single source, single wavelength. This could limit its use for monitoring to minutes or hours as opposed to days.

Thus, for the above reasons, among others, there is a need for a single probe apparatus or device which can provide high quality information, which is stable, i.e., without time sharing between Fluorimeter and Reflectometer about viability of tissue by monitoring at least two or more parameters at the same time, on the same tissue volume, without possible perturbations or interferences between the different input or output signals, respectively, distorting the information.

SUMMARY OF THE INVENTION

It has been found that such a device that can monitor simultaneously, in the identical volume element of tissue, both the redox state (NADH) and blood velocity, can be built, without these measurements causing possible perturbations or interfering with each other, by using a single radiation source.

Since, in order to correlate the redox state (NADH) with the tissue blood flow it is necessary to use the same tissue volume element connected to the bundle of optical fibers, a Y-shape light guide is used for the transmission of light to and from the organ under observation.

The entire reflected light from the tissue is split and used for monitoring the various parameters. Another option is to split the fibers collecting light from various areas but then the correlation will not be as good when one bundle is used for all signals. To optimize the construction of the light guide we are using quartz fibers 240 microns including the cladding. This will provide the best utilization of the area of the bundle (packing fraction) and also will be flexible. The glue used for the fibers must be non-fluorescing or reacting when light is shed on the fibers. Preferably, use is made of crazy glue made by Elmer Company (Cyanoacrylate glue).

This arrangement of a combined instrument and especially combined fiber optic probe has advantages in monitoring tissue energy state as compared to the current available techniques.

a. The unit utilizes one wavelength and one light source for both measurements; i.e., smaller probe, less bulky electronics, no possibility of perturbations or interferences and more stability.

b. The information collected for the various parameters calculated originate from the same volume element of tissue (horizontal and vertical).

c. The correlation between the various parameters serves as a basic tool to calculate the viability of the tissue.

According to the present invention, there is provided an apparatus which monitors both the redox state (NADH) and blood velocity (MBF) of the same tissue volume element comprising:

a single radiation source (e.g., 366 or 324 mm);

a probe consisting of a bundle of fibers said lightguide shaped in a Y which transmits light to and from tissue;

a light splitter which takes an adequate portion of the reflected light for (NADH) determination and directs the balance for blood velocity determination (MBF);

a fluorometer—a photo multiplier tube with a suitable filters (e.g., 450 nm);

a Doppler Analyzer—with a suitable filter (e.g., 380 nm cutoff);

(optionally) a reflectometer—a photo multiplier tube with a suitable filter (e.g., 366 nm or 324 nm) the above constituting a single signal-single probe multiparameter monitor, or Metaflow Probe (MFP), combined with a computer based expert system comprising, inter alia, an analog to digital converter to convert the analog signals from the fluorometer, reflectometer and Doppler Analyzer to create a digital file in the computer.

This apparatus constitutes a Tissue Energy State Analyzer which provides reliable information on the energy state (NADH) (via fluorometry, F) normalized both for blood flow (via Doppler Analyzer, DA) and blood volume (via reflectometry, R) of the tissue.

Alternatively, the single probe multiparameter monitor (i.e., Metaflow probe, MFP) can be combined with two isolated Pt wires and an amplifier to additionally monitor the spontaneous electrocortical activity (ECoG) in the region of the volume dement under study, said signals transferred to the expert system for quantitative analysis, this combined MFP and ECoG dual signal constituting a Brain Viability Probe, which can be used to evaluate brain viability in the operating room.

Another alternative is to combine the Brain Viability Probe with sensors which monitor other parameters in the region of the volume element under study, such as:

- a fiber optic probe, or another suitable probe, connected to a pressure transducer to monitor Parenchymal pressure (ICP—intracranial pressure);
- a $K^+$ mini-electrode and reference electrode connected to an electrometer to monitor extracellular $K^+$ and dc potential;
- a thermistor probe connected to a telethermometer to monitor local brain temperature;
- the signals being transferred to the expert system for analysis, said system comprising a Brain Functions Analyzer, to evaluate the functional state of the brain during relatively long periods (hours to two days).

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1A:
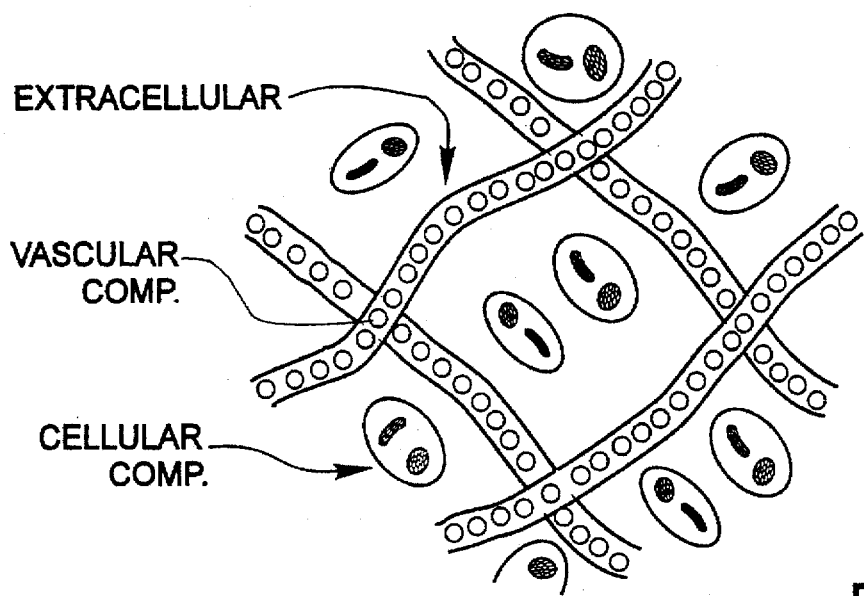
FIG. 1A. Schematic presentation of the various tissue components
Figure 2:
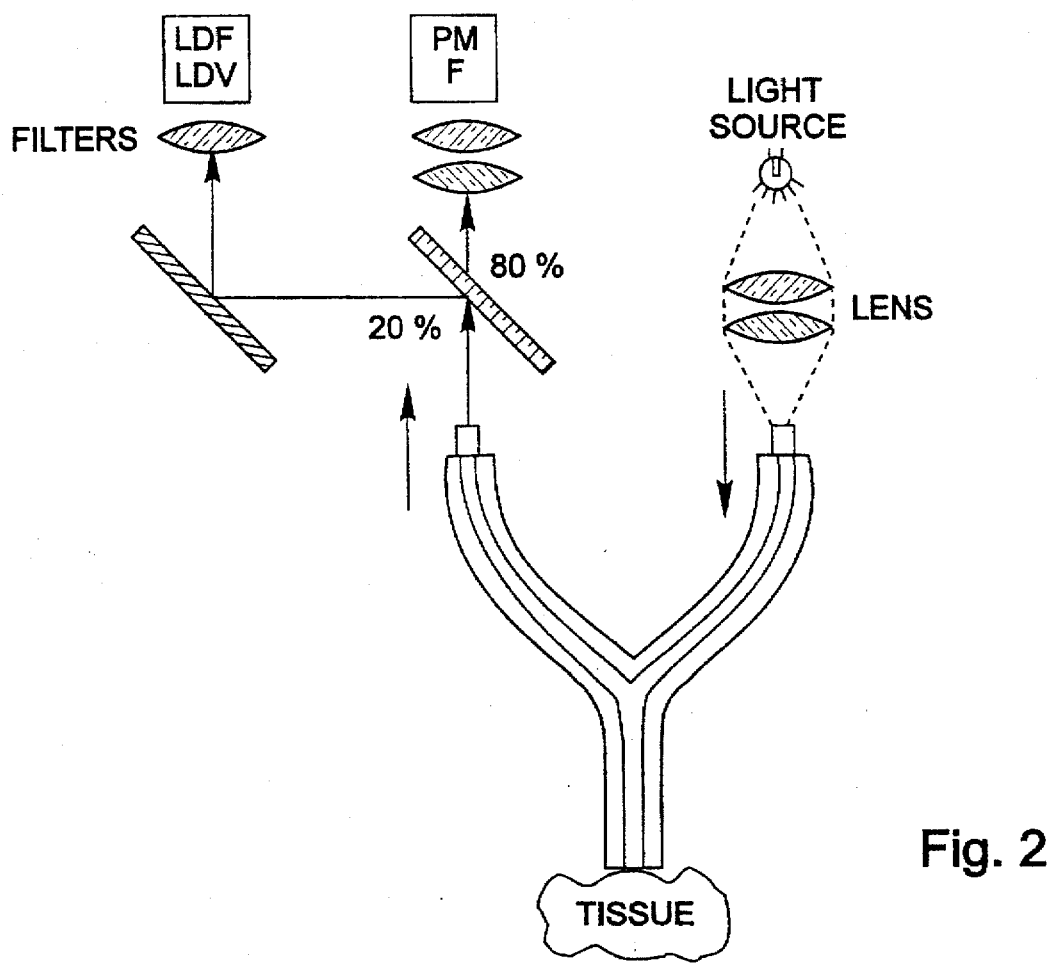
FIG. 2. Schematic presentation of the principle components of the single-signal-single probe multiparameter analyzer, Metaflow Probe, F-fluorometer, LDF—Doppler Flowmetry.
Figure 1B:
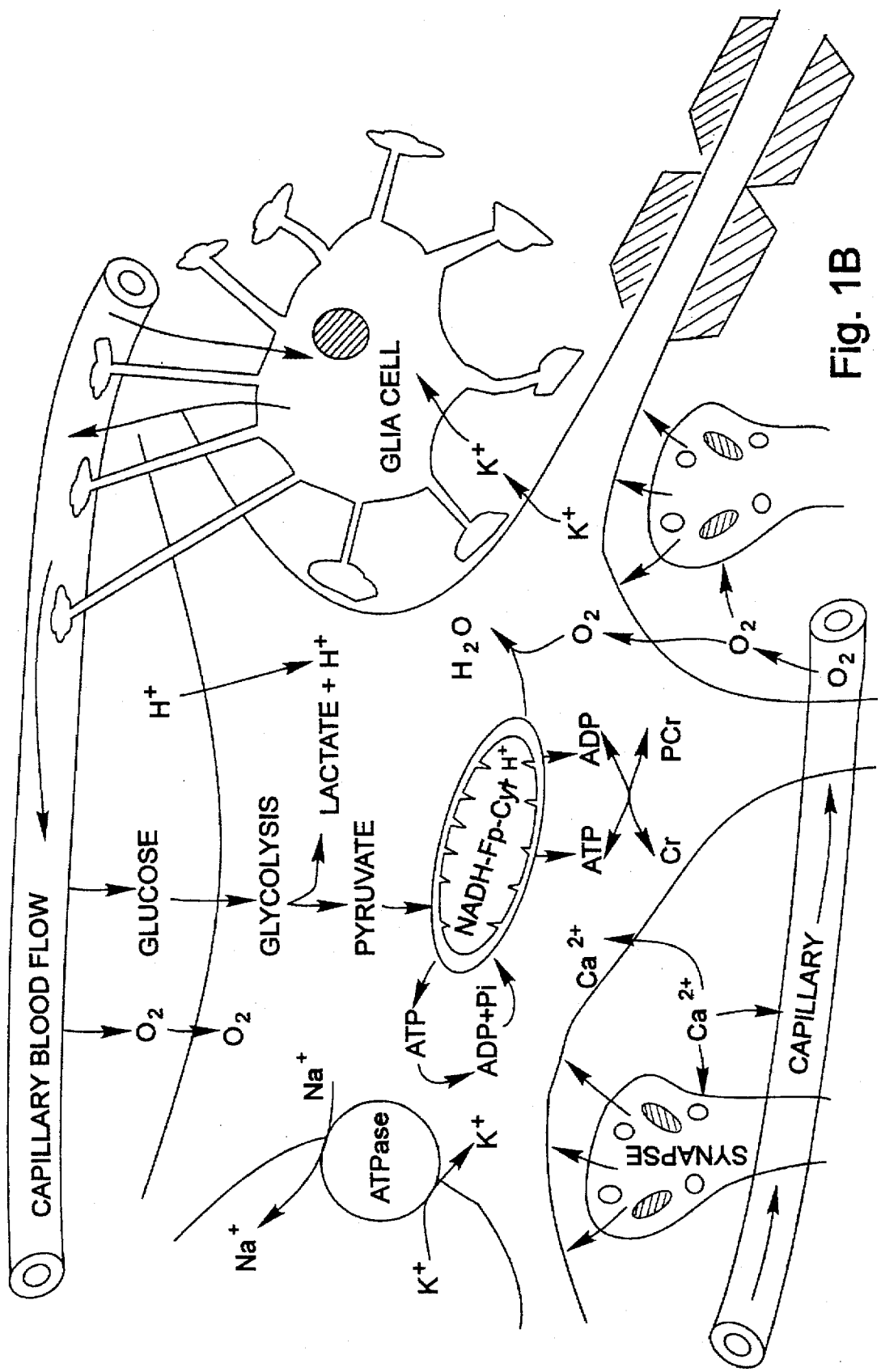
FIG. 1B. Schematic presentation of a neuronal tissue showing the interrelation between neurons, glial cell and blood vessels.
Figure 1C:
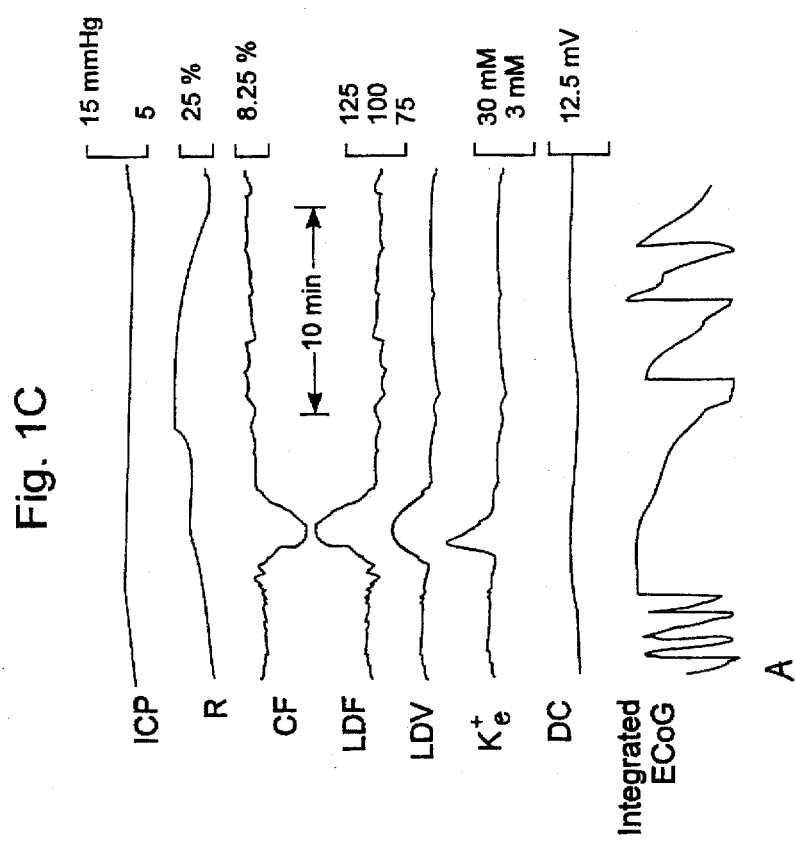
FIG. 1C. Spontaneous depolarization waves (spreading depression) developed in a patient after severe head injury. Part A shows typical normal response while the response shown in B is typical of a brain after microcirculatory disturbances based on animal experiments (Mayevsky, A., Zarchin, N., and Freidli, C. M., Factors affecting the oxygen balance in the awake cerebral cortex exposed to spreading depression, Brain Res. 236:93–105 (1982)).
Figure 1D:
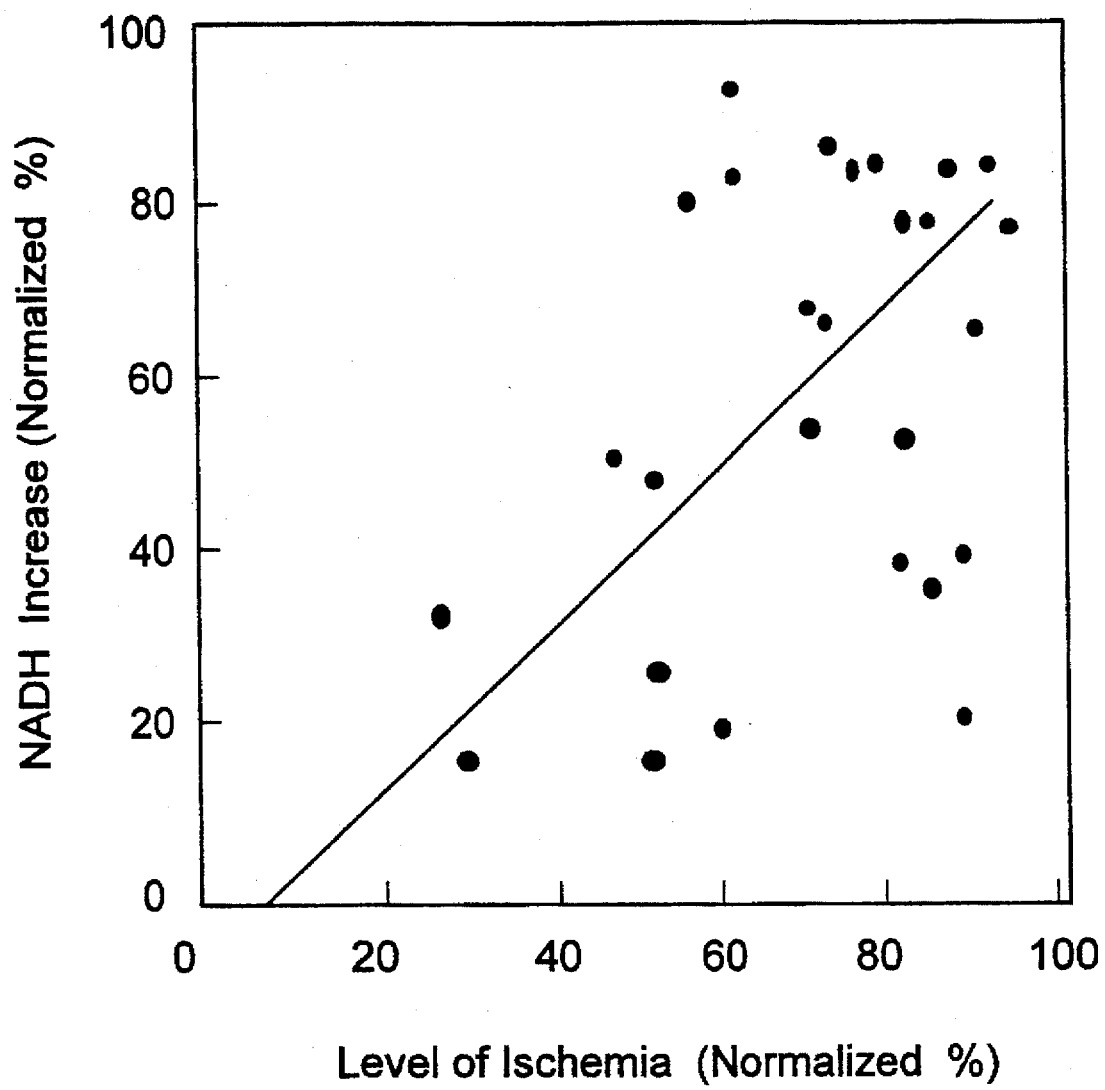
FIG. 1D. The correlation between the level of ischemia (carotid artery occlusion) and the NADH response in the Mongolian gerbil. Each point represents one occlusion and the values were normalized in the 0–100% range of each parameter.

A preferred embodiment of the invention as illustrated in FIG. 2, comprises:

- a single radiation source; e.g., a Mercury lamp (366 nm) or Laser (He-Cd [324 nm]);
- a Y-shaped light guide probe, consisting of optical fibers;
- a fluorometer to measure fluorescence peaked at about 450 nm light splitters and filters; and
- a Doppler Analyzer;

The principle of (NADH) monitoring from the surface of the tissue is that excitation light (366 or 324 nm) is passed from the fluorometer to the tissue via a bundle of optical fibers made of quartz (FIG. 2). The emitted fluorescent light peaked at 450 nm (about 420 to about 480 nm) together with the reflected light at the excitation wavelength, is transferred to the fluorometer via another bundle of fibers, being first split in an 80:20 ratio before entry into the fluorometer. An appropriate filter is located in from of the photomultiplier to provide the (NADH) signal.

The other 20% of the light is used for the measurement of tissue blood flow using the principles of Laser Doppler Flowmetry. The frequency change which light undergoes when reflected by moving red blood cells is the basis for this measurement. After the multiple scattering of the excitation light the reflected light is transmitted to the photo detector. The run signal is analyzed by an appropriate algorithm in a computer based expert system, comprising, inter alia, an analog to digital converter, to create a digital file in the computer and the results are presented in percent of a full scale (0–100%) providing relative flow values.

Figure 3A:
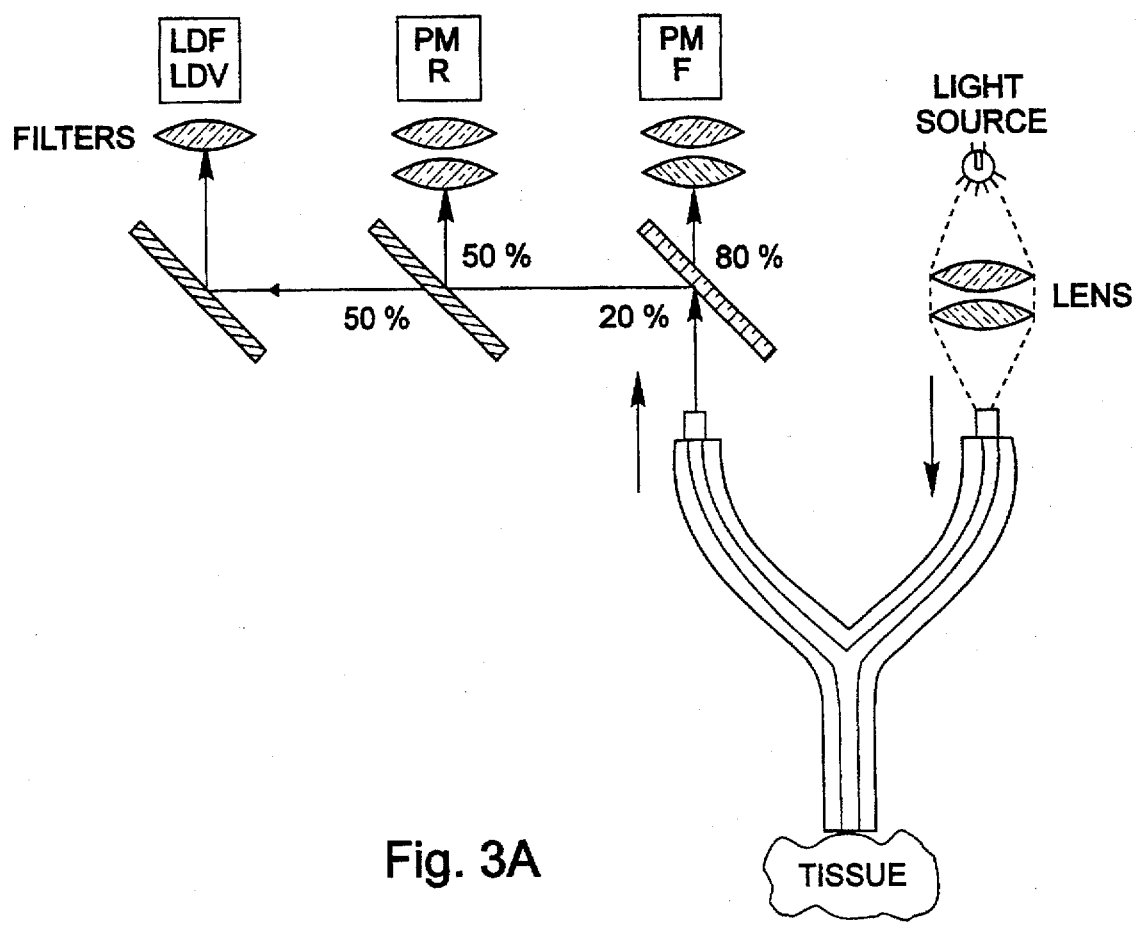
FIG. 3A. Same as 2, with the inclusion of a second light splitter, and a reflectometer, R.

A more preferred embodiment of the invention as shown in FIG. 3A, comprises the addition of a reflectometer (R) to the fluorometer (F), and Doppler Analyzer (DA) of FIG. 2, capable of generating three signals; i.e., from F, from R, and from DA.

The emitted fluorescent light peaked at 450 nm (about 420 to about 480 nm) together with the reflected light at the excitation wavelength, is transferred to the fluorometer via another bundle of fibers, being first split into a 80:20 ratio before entry into fluorometer. The beam of light is split again in a 50:50 ratio to provide a reflectance signal at the excitation wavelength. Appropriate filters are located in front of the two photomultipliers to provide the NADH signal as well as the reflectance signal. The changes in the reflectance signal represent changes, inter alia, in the microcirculatory blood volume (MBV) and could be used to correct the fluorescence signals for hemodynamic or other absorption changes taking place in the tissue under various perturbations. (See, Mayevsky, A., Brain NADH redox state monitored in vivo by fiber optic surface fluorometry, Brain Res. Rev. 7: 49–68, (1984).)

The other 50% (10% of the original reflected signal) of the reflected light is used for the measurement of tissue blood flow using the principles of Laser Doppler Flowmetry. The frequency change which light undergoes when reflected by moving red blood cells is the basis for this measurement. After the multiple scattering of the excitation light the reflected light is transmitted to the photo detector. The run signal is analyzed by appropriate algorithm in a computer based expert system, comprising an analog to digital converter to create a digital file in the computer and the results are presented in percent of a full scale (0–100%) providing relative flow values. This apparatus constitutes a Tissue Energy State Analyzer (TESA).

Example 1—Tissue Energy State Analyzer

Figure 3B:
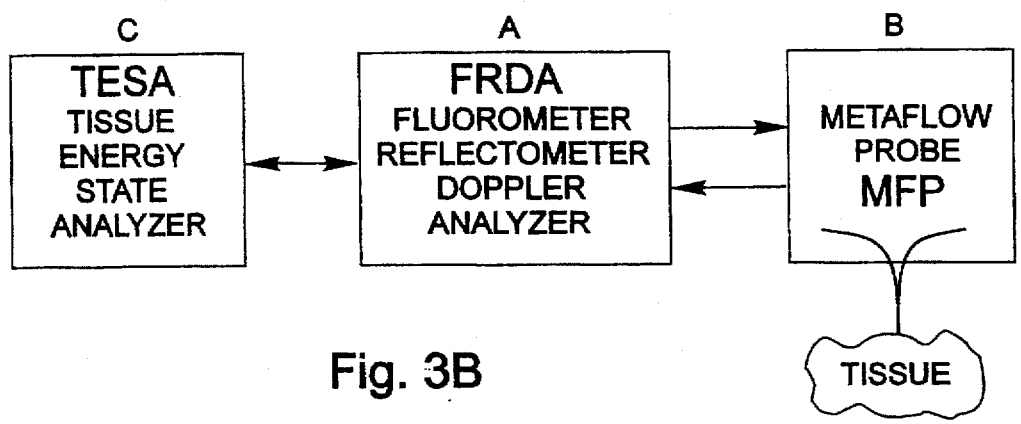
FIG. 3B. Schematic of various components of Tissue energy State Analyzer.
Figure 3C:
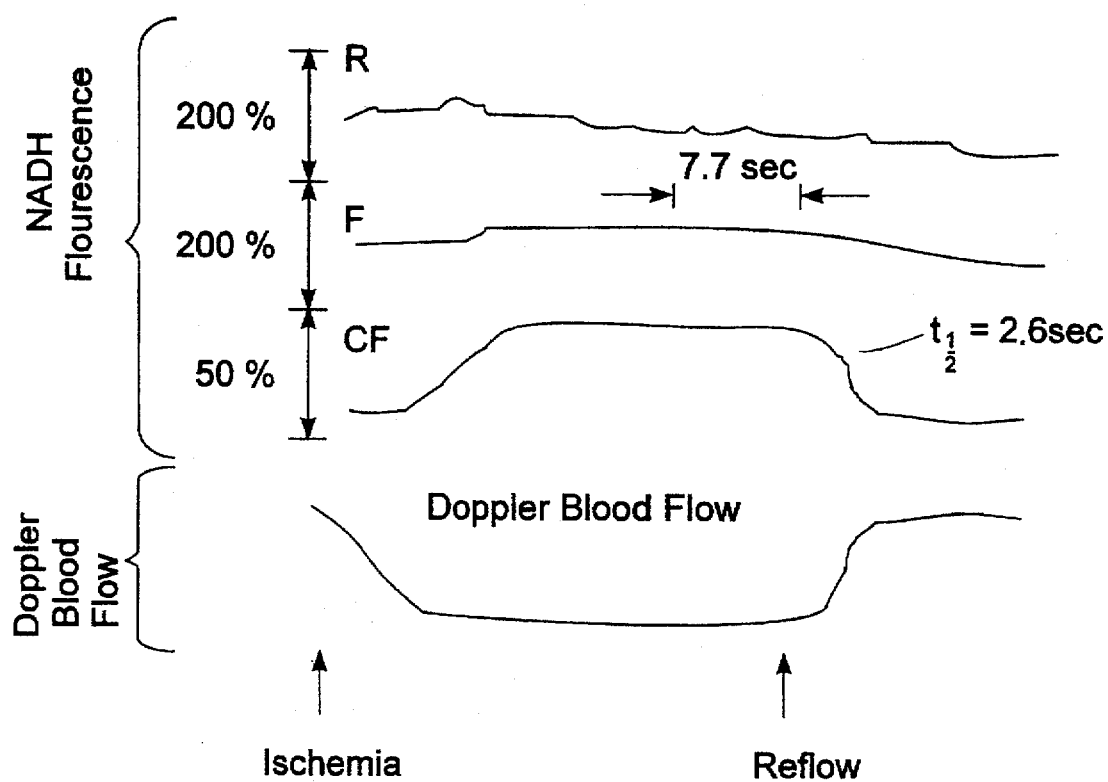
FIG. 3C. Effects of carotid artery occlusion in adult human brain—observation made in cerebral cortex intraoperatively.

This unit contains a computer-based expert system to provide real time evaluation of tissue energy state. The analog signals measured by the Fluorometer Reflectometer Doppler Analyzer (FRDA) (see FIG. 3B) are transferred to an analog to digital convertor to create a digital data file in the computer. Each of the signals is defined in terms of minimal and maximal values to provide the dynamic range. After placing the probe on the tissue, the baseline values of all the parameters are determined. In order to identify the energy state of the tissue it is necessary to perturb it by a known stimulus and the response is recorded. Since the monitored signal could not be calibrated in absolute values, the perturbation is a necessary step in determination of the energy state. A practical non-damaging perturbation in cases of organ transplantation, is a very short occlusion of blood vessel supplying the monitored area. Such a short ischemia will induce a decrease in blood flow and an increase in redox state (more NADH and less NAD) as seen in FIG. 3C for the human brain as an example. Based on the size of changes due to the perturbation the expert system is able to locate the energy state of the tissue in the 0–100% range. The time it takes these perturbed signals to return halfway back to their non-perturbed values, $t_{1/2}$, is an important parameter representing the oxygenation potential of the tissue, which is easily measured in this manner. Another possible perturbation is an injection of a known effective drug to the organ tested to change its activity. The response of the organ to the injection is compared to the statistical calculated response.

TABLE 1

Tissue Energy State Index

|  | Reflectance | NADH | Blood Flow | Blood Volume | TESI |
|---|---|---|---|---|---|
| Normoxia | 100% | 100% | 100% | 100% | 100 |
| Ischemia-100% | 100–150 | 200 | 0 | 50 | 0 |
| Ischemia-50% | 100–150 | 150 | 50 | 50–100 | 50 |
| Hyperoxia | 110–120 | 90–80 | 90–80 | 90–80 | 120 |

Another preferred embodiment of the invention comprises, (see FIG. 4), a single radiation source (e.g., 366 or 324 nm);

a light splitter;

light filters;

a fluorometer;

a reflectometer;

a Doppler Analyzer;

a probe comprising the combination of optical fibers with a pair of isolated Pt electrodes connected to an ac signal amplifier, the above constituting a Brain Viability Probe;

combined with a computer based expert system, comprising, inter alia an analog to digital converter to convert the analog signals to create a digital file in the computer.

Figure 4:
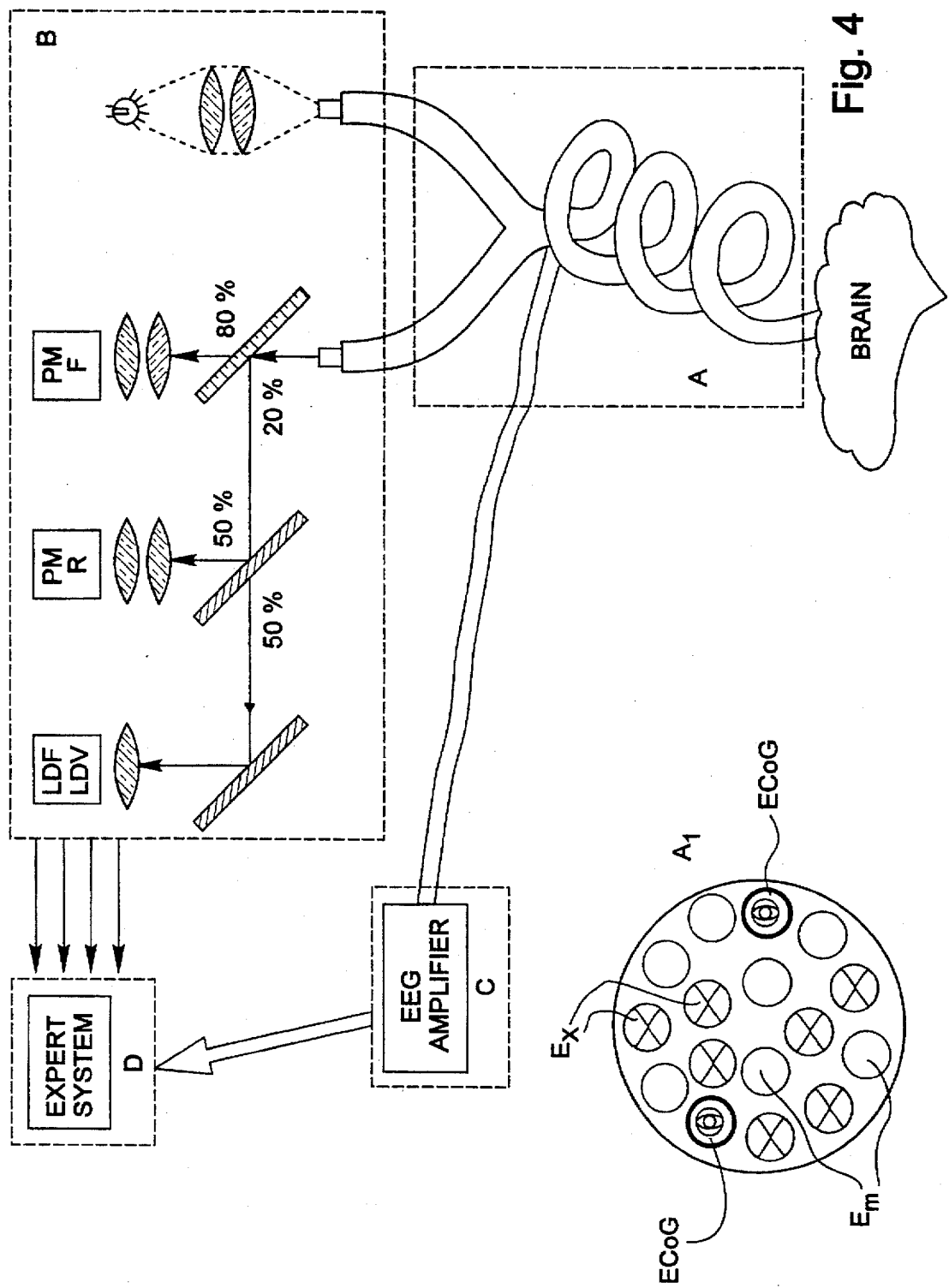
FIG. 4. Schematic presentation of the Brain Viability Analyzer.

This probe contains two groups of optical fibers mixed randomly (for NADH and MBF monitoring) as well as two insulated platinum wires for ECoG measurement. The common end of this Brain Viability Probe BVP is polished and the view of its cross section is shown in FIG. 4. The length of the common end (A) can vary according to the specific needs and signal attenuation is negligible in range of up to 10 meters. The possibility to build the flexible common end with a 2–3 mm diameter made the BVP practical tool to be used in the neurosurgical operating room. The BVP is held by a micromanipulator to be connected to the standard neurosurgical head holder. The BVP is placed on the surface of the brain and the monitoring time will be in the range of 5–60 mutes depending on the surgical procedure. This apparatus constitutes a Brain Viability Analyzer (BVA).

Example 2—Brain Viability Analyzer (BVA)

This computerized system receives the output as five separate signals:

1. (NADH) fluorescence;
2. 324 reflectance;
3. MBF;
4. MBV;
5. ECoG.

The calibration of the ECoG signal is in absolute units, namely, in amplitude (microvolts) as well as frequency (cycles/see). Fast Fourier Transform (FFT) analysis is used to analyze the signal and provide quantitative measure for real-time evaluation of the ECoG changes. The ECoG parameters which can be used are spectral Edge frequency as well as total amplitude of the signal. The other four parameters are calibrated in relative units only. Thus, after positioning of the probe on the brain the signal is calibrated to provide a known electronic value defined as 100% of signal (control base line signal). All changes in those four signals are calculated relative to the control value and presented as percent changes.

In order to calculate the Brain Viability Index (BVI) the expert system analyzes the five measured parameters in real time and uses the preloaded database for the evaluation of the viability state of the brain. This database was created by a large number of animal experimental results, as well as preliminary human brain results. This database will be dynamically updated as more results in humans and animals are accumulated. Table 2 shows five typical responses of the brain to known perturbations as compared to the normoxic brain.

TABLE 2

Brain Viability Index - BVI calculated by the relative changes in the 5 related parameters measured by the brain viability probe and analyzer.

| Perturbation | Reflectance | NADH | CBF | CBV | ECoG | BVI |
|---|---|---|---|---|---|---|
| Normoxia | 100 | 100 | 100 | 100 | 100 | 100 |
| Ischemia (100%) | 100–150 | 200 | 0 | 50 | 0 | 0 |
| Ischemia (50%) | 100–150 | 150 | 50 | 50–100 | 60–40 | 50 |
| Hypoxia (50%) | 60–80 | 150 | 150–200 | 150 | 60–40 | 50 |
| Anoxia | 50–60 | 200 | 50–150 | 130–150 | 0–10 | 0 |

As seen the BVI range is from 0 (ischemic, anoxic or dead brain) through the normal brain (100 BVI). The level of 110–120 in the activated brain or under hyperoxic conditions could be reached (not shown in the Table). The differentiation between two or more situations having the same BVI is done by comparing the relative changes in the various parameters. For example, differentiating between states 3 and 4 having identical change in (NADH) and BVI is based on the difference in the calculated values of the reflectance, MBF and MBV.

Figure 5:
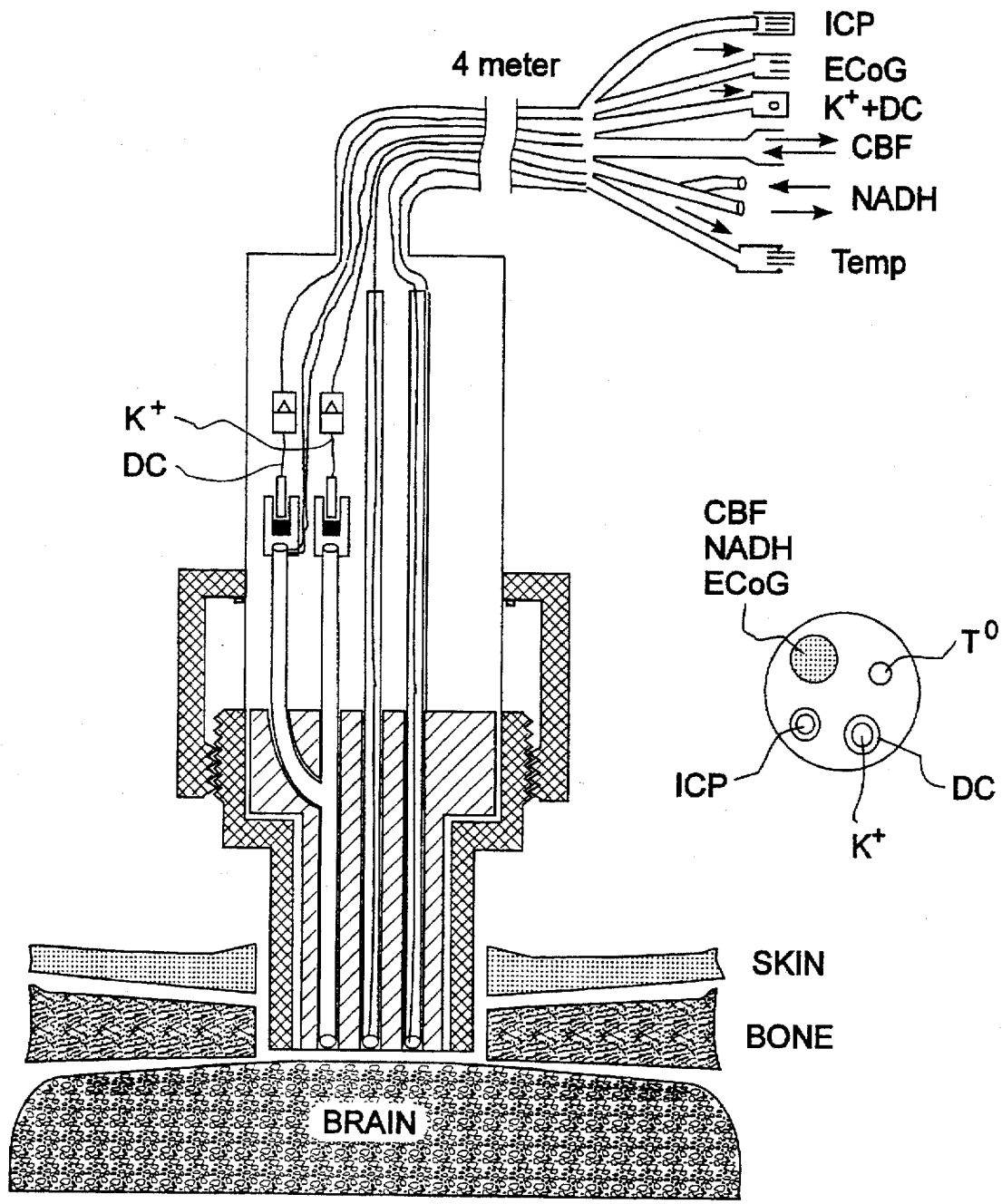
FIG. 5. Schematic presentation of a longitudinal section of the Multiprobe Assembly, MPA used for human brain monitoring.
Figure 6:
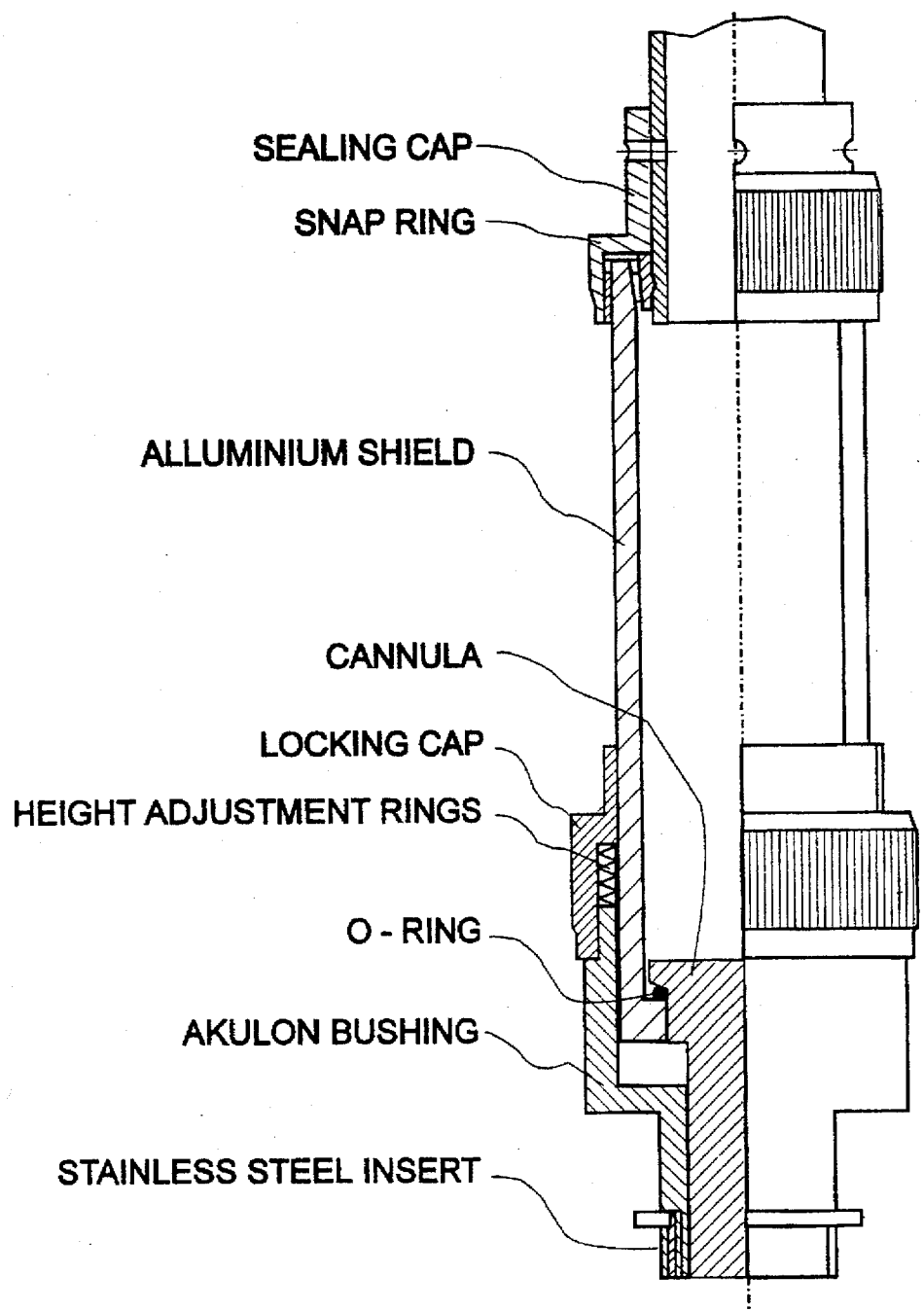
FIG. 6. Longitudinal section of the MPA together with its connection assembly to the skull of a patient's head.

Another preferred embodiment of the invention, comprises, (see FIGS. 5 and 6):

a Brain Viability Probe, described in Example 2;

a fiber optic probe connected to a pressure transducer to measure parenchymal pressure;

a $K^+$ electrode/reference electrode connected to an electrometer to monitor extracellular $K^+$ ions concentration and dc potential;

a thermistor probe connected to a telethermometer to monitor local temperature;

the above constituting a Multiprobe Assembly (MPA);

combined with an expert computer system, comprising, inter alia, an analog to digital convertor to convert the analog signals to create a digital file in the computer.

This apparatus constitutes a Brain Function Analyzer (BFA).

Example 3—Brain Function Analyzer

In order to evaluate the functional state of the brain during long term periods (few hours to two days) the strategy of the monitoring approach must be different as compared to the BVA described above. In patients exposed to severe head injury or during the early postoperative period the following parameters are monitored from the surface of the brain:

1. Tissue blood flow and volume (using Laser Doppler flowmeter);
2. Intramitochondrial redox state (NADH fluorometry);
3. Extracellular level of $K^+$ (surface minielectrode);
4. Direct current (dc) steady potential (Ag/AgCl electrode);
5. Intracranial Pressure (using, for example, a Camino probe);
6. Electrocorticography (bipolar cortical electrodes);
7. Tissue Temperature (surface Thermistor).

All the probes are assembled in a special design multiprobe assembly (MPA). See FIGS. 5 and 6. Since more than 50% of the energy consumed by the brain is used by the active transport processes it is important to monitor the ionic homeostasis by the $K^+$ electrode. The analyzer of brain functions is an extension of the brain viability analyzer described above.

Figure 7:
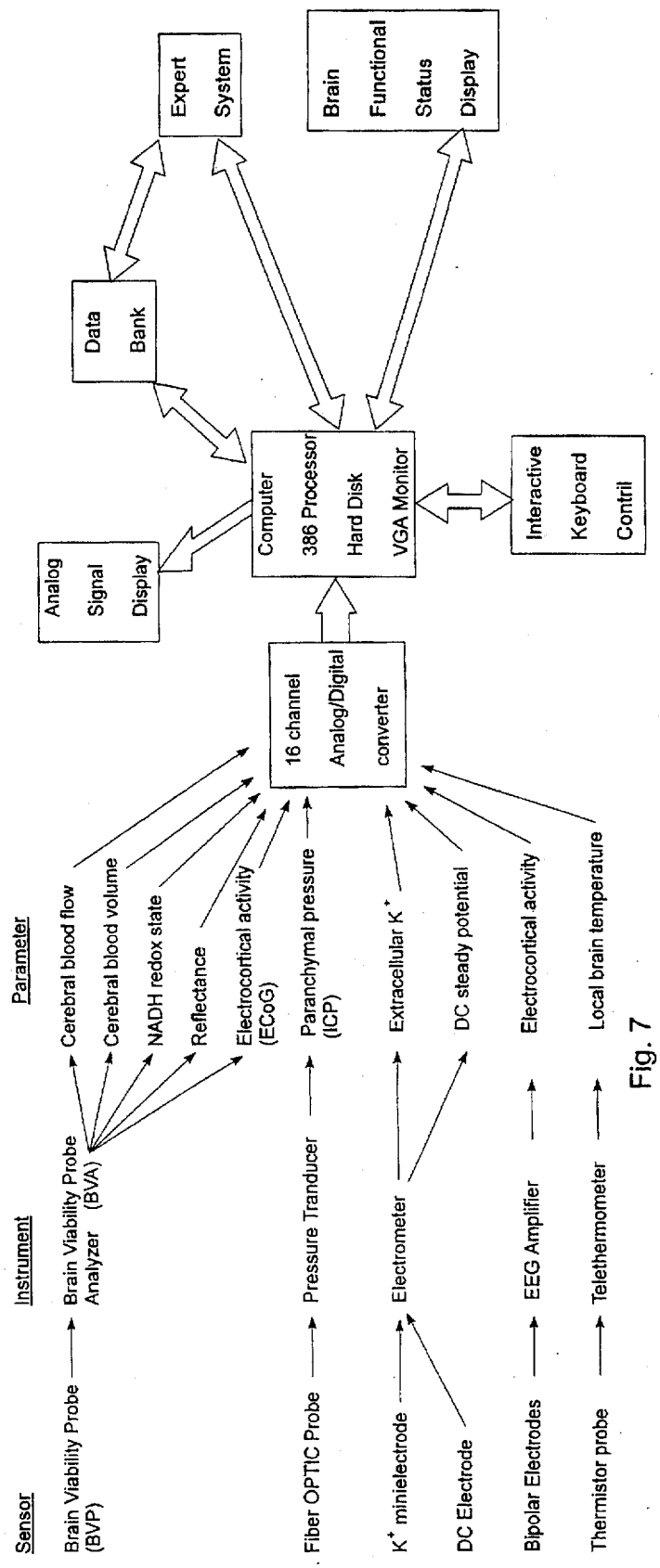
FIG. 7. Schematic presentation of Brain Function Analyzer.

FIG. 7 shows the various components of the BFA including the expert system and the display of the Brain Functions Index (BFI). As seen, the various parameter monitored are sampled and the real time values are used by the expert system to calculate the BFI. It is to be noted that the BFI is a continuous function with all values between 0 and 100 possible.

Table 3 shows the effects of 9 different perturbations on the BFI as compared to the normoxic value CBFI—100).

TABLE 3

Brain Function Index - BFI calculated by the relative changes in the 9 related parameters measured by the brain multiprobe assembly and analyzer.

| Perturbation | Reflectance (%) | NADH (%) | CBF (%) | CBV (%) | ECoG (%) | K mM | DC mV | mm Hg | Temp °C. | BFI |
|---|---|---|---|---|---|---|---|---|---|---|
| 1 Normoxia | 100 | 100 | 100 | 100 | 100 | 2–5 | 0 | 0–10 | 36–37 100% | 100 |
| 2 Ischemia (100%) | 100–150 | 200 | 0 | 50 | 0 | >15 | >(−5) | >15 | <36 | 0 |
| 3 Ischemia (50%) | 100–150 | 150 | 50 | 50–100 | 60–40 | 2–12 | 0–(−5) | 0–20 | <36 | 50 |
| 4 Hypoxia (50%) | 60–80 | 150 | 150–200 | 150 | 60–40 | 2–12 | 0–(−5) | 0–20 | >36–37 | 50 |
| 5 Anoxia | 50–60 | 200 | 50–150 | 130–150 | 0–10 | >12 | >(−5) | >15 | >36–37 | 0 |
| 6 Spreading Depression (SD) | 130←→50 | 80 | 200 | 80←→150 | 20–30 | >12 | >(−5) | 0–10 | >36–37 | 130 |
| 7 SD (Ischemia) | 150 | 120 | 50–70 | 50 | 20–30 | >12 | >(−5) | 0–10 | <36 | 80 |
| 8 Epilepsy | 80–90 | 90 | 120–150 | 120 | 150–200 | 2–12 | 0–(−10) | 0–20 | >36–37 | 110–120 |

TABLE 3-continued

Brain Function Index - BFI calculated by the relative changes in the 9 related parameters measured by the brain multiprobe assembly and analyzer.

| Perturbation | Reflectance (%) | NADH (%) | CBF (%) | CBV (%) | ECoG (%) | K mM | DC mV | mm Hg | Temp °C. | BFI |
|---|---|---|---|---|---|---|---|---|---|---|
| 9 Epilepsy + SD | Time Depend. 8→6 | | | | | >12 | >(-5) | 0-20 | >36-37 | 110←→130 |
| 10 Hyperoxia | 110-120 | 90-80 | 90-80 | 90-80 | 90 | 2-5 | 0 | 0-10 | <36 | 110-120 |

Figures 8A, 8B:
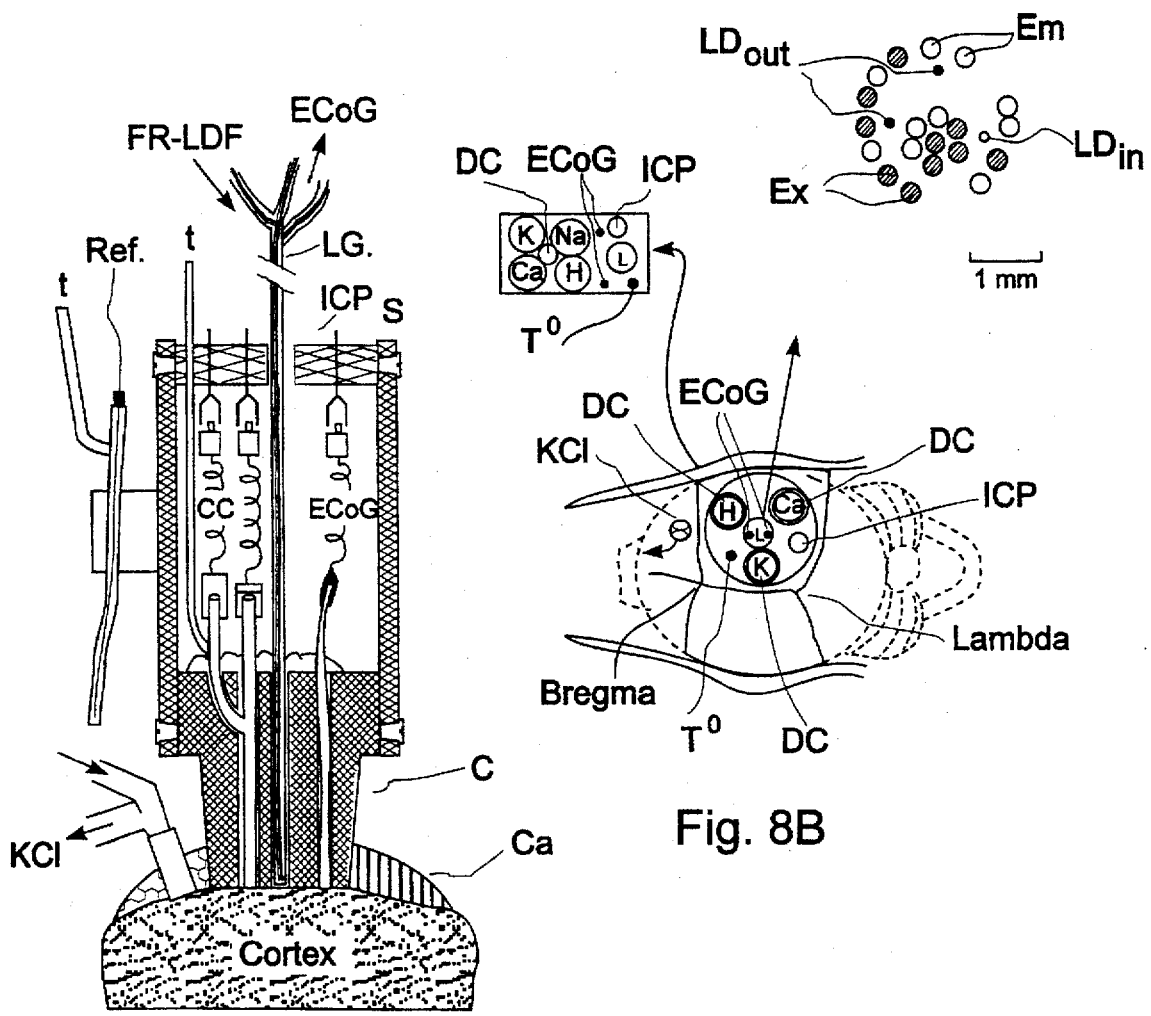
FIG. 8A. Pictorial representation of the multiprobe apparatus of the present invention, partially in cross-section, configured for experimental animal or human monitoring of brain functions in real time.
FIG. 8B shows a cross-sectional plan view taken through line 2—2 of the combined light guide apparatus of the old version of MPA (Mayevsky, A., Flamm, E. S., Perrole, W. and Chance, B., A fiber optic based multiprobe system for intraoperative monitoring of brain functions. SPIE Proc. Vol 1431:303–313 (1991)). In the present invention the same bundle of fibers is used for the monitoring of CBF and NADH redox state as well as probes for the other parameters.

A preferred embodiment of the multiprobe assembly is shown in FIG. 8A. For illustrative purposes, the multiprobe assembly of the present invention will be described in a configuration used to monitor, cerebral blood flow, —NADH redox state and extracellular ($K^+$, $Ca^{2+}$, $H^+$ and $Na^+$) ion concentrations within the brain, although the multiprobe assembly could more generally be used to monitor other brain activities and may be simplified, as explained below.

Referring to FIG. 8A, the multiprobe holder, which is preferably made of Delrin or similar plastic material, contains a bundle of optical fibers, three ion specific electrodes, each combined with a surrounding dc steady potential electrode, electrocortical electrodes (shown in FIG. 8B), and a reference electrode. The ion selective electrodes are electrically connected to Ag/AgCl electrode holders that are protected by a plexiglass sleeve.

The optical fiber bundle according to the present invention, also known as a light guide, includes a single optical fiber bundle shown generally in FIG. 8A which serves to conduct radiation used in both the blood flow measurement and the NADH redox state. Two different alternative fiber bundle configurations are shown in FIG. 8A, one in place and another in the inset.

Further details of the multiprobe assembly are preferably arrayed around the light guide. The solution adopted for the electrode holder is basically a modification of the Lucite cannula described by Mayersky et al. (Mayersky, A., Crowe, W. and Mela, L., The interrelation between brain oxidative metabolism and extracellular potassium in the unanesthetized gerbil, Neurol. Res. 1:213-226 (1980)), for the light guide and the potassium-sensitive electrode. To offer space for more probes, the new cannula is shaped as a truncated cone instead of a cylinder. The holes accommodating short electrode probes ($K^+$, $Ca^{2+}$, $Na^+$ or $H^+$) made convergent toward the lower surface to occupy less space on the brain and divergent at the top to facilitate handling and sealing of the probes (Friedli, C. M., Solarsky, D. S. and Mayersky, A., Multiprobe monitoring of ionic, metabolic and electrical activities in the awake brain. Am. J. Physiol, 243: R462-R469 (1982); Mayevsky, A., Multiparameter monitoring of the awake brain under hyperbaric oxygenation, J. App. Physiol. 54:740-748 (1983)). An additional hole is drilled obliquely form the upper surface to merge with each sensor channel at about mid-distance of the lower surface. This hole accommodates an polyethylene tubing used to record the local dc potential concentrically to the sensor.

The long and rigid steel stem of the light guide (L) used in this study occupies a straight vertical hole in the cannula and serves as an axis to hold the cannula (c) and the cable holder (h) at a convenient distance of each other. Steel rods (preferentially threaded) can be used as additional or replacement pillars to fix the cannula to the cables holder. The arrangement leaves optimal access to the electrodes and electrical connections for assembling and replacement. The complete assembly is protected and shielded by a sliver-pointed Lucite or aluminum sleeve sliding over the cable holder. If a stronger construction is desired, the sleeve can also be permanently screwed into the cannula and cable holder, with a half-cylinder piece cut out as a removable cover.

When the holder is assembled, the fixed steel pillars are screwed and/or glued in first. To avoid tension on the electrodes wires, they are connected to the input cable through a flexible coil of 36-gauge isolated copper wire (Belden).

Once the electrodes are in place, the dc channel and the lower part of the sensor channel are filled with fluid from a lateral hole connected to a reservoir syringe. Thus, it can be ensured that each sensor and dc electrode is tightly sealed to the top of the cannula and will not let saline reflow back into the cable housing compartment. The system also allows the extracellular fluid and blood to be cleaned from the slit around each probe after the cannula is removed from an implantation site. In the final assembly, a protective sleeve is used as an anchoring point for the refill tubes to the dc and sensor channels (f) and for the reference liquid junction (REF).

Also disposed within the optical fiber bundle which is located in the multiprobe assembly are electrocortical electrodes which are fed to an EEG amplifier, a fiber optic probe (shown in FIGS. 8A and 8B) connected to a pressure transducer for monitoring parenchymal pressure, and a thermocouple electrode for monitoring temperature. Adjacent the multiprobe assembly is the push-pull cannula for application of KCl in order to activate the animal's brain. The electrodes of the multiprobe assembly are preferably held to the cannula using epoxy glue so that the multiprobe assembly can be used during the awake state or to avoid artifacts in the operating room environment. In the experimental apparatus embodiment, as shown in FIG. 8A, dental acrylic cement, or a similar material, was used to non-invasively interface the multiprobe assembly to the surface of the cortex by cementing it to the skull. In certain embodiments, the multiprobe assembly can be removed without damage from the brain at the end of the measurements and repetitive applications can be performed in a short period of time with minimal technical support. Furthermore, such non-invasive surface contact with the tissue permits for monitoring of the human brain. The multiprobe assembly is most preferably located on the exposed cortex using a micromanipulator.

Based upon animal experiments, it has now been found that a more preferable embodiment of the multiprobe analyzer may be available for monitoring under the complex conditions of the operating room environment, this embodiment requires only four probes. In order to monitor the functional state of the human brain, it would be necessary to include at a minimum an FRDA apparatus (FIG. 3B) which includes a laser Doppler flowmeter discussed above to measure relative cerebral blood flow and a fluorometer/ reflectometer system to monitor the intramitochondrial NADH redox state, the potassium ion (K$^+$) specific electrode to provide data on the extracellular level of K$^+$ ions, on the temperature, and a fiber optic probe to measure parenchymal pressure.

Figure 10A:
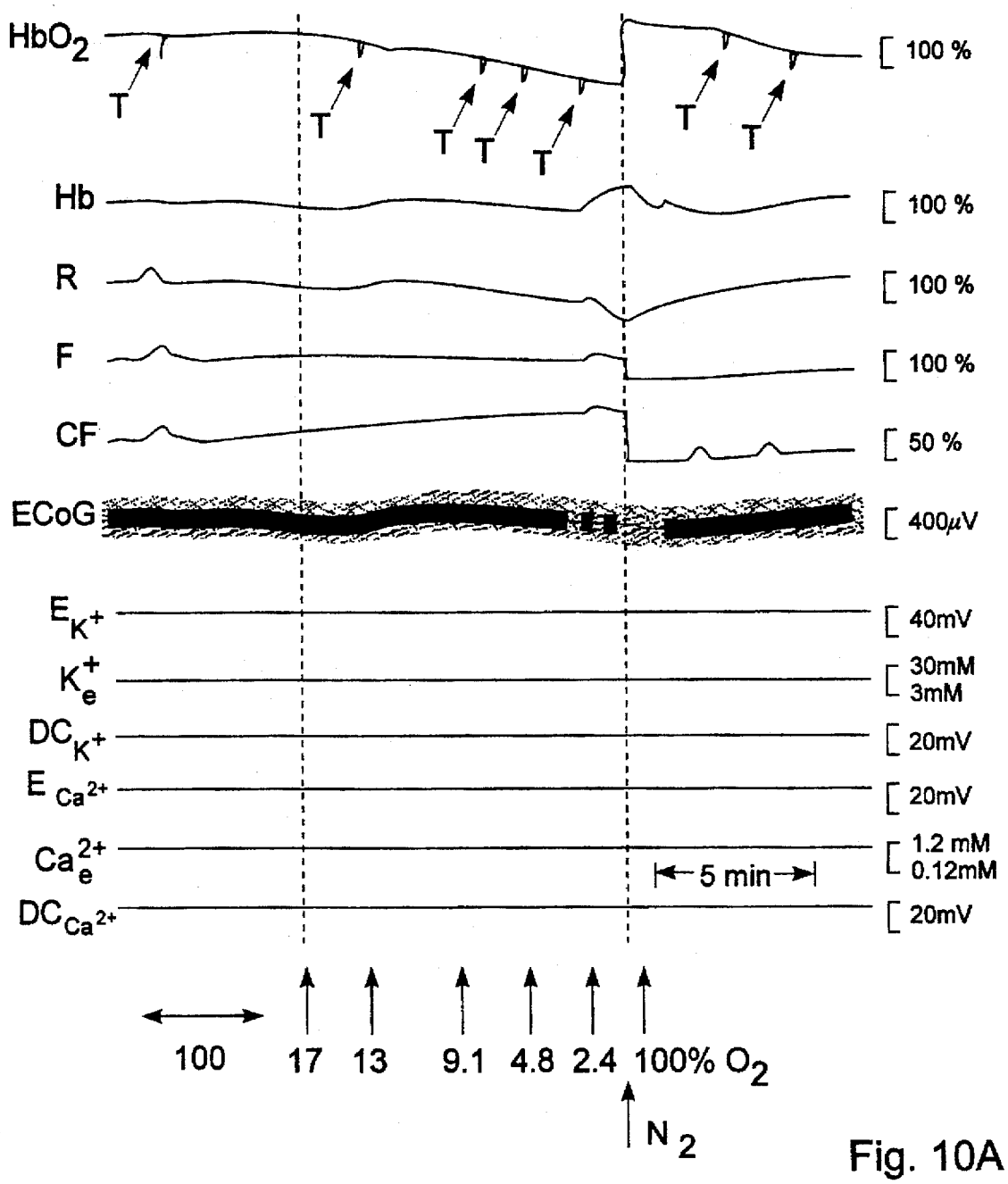
FIG. 10A is a plot of, inter alia, NADH redox state (CF) and hemoglobin saturation ($HbO_2$) for an animal undergoing an episode of hypoxia.
Figure 10B:
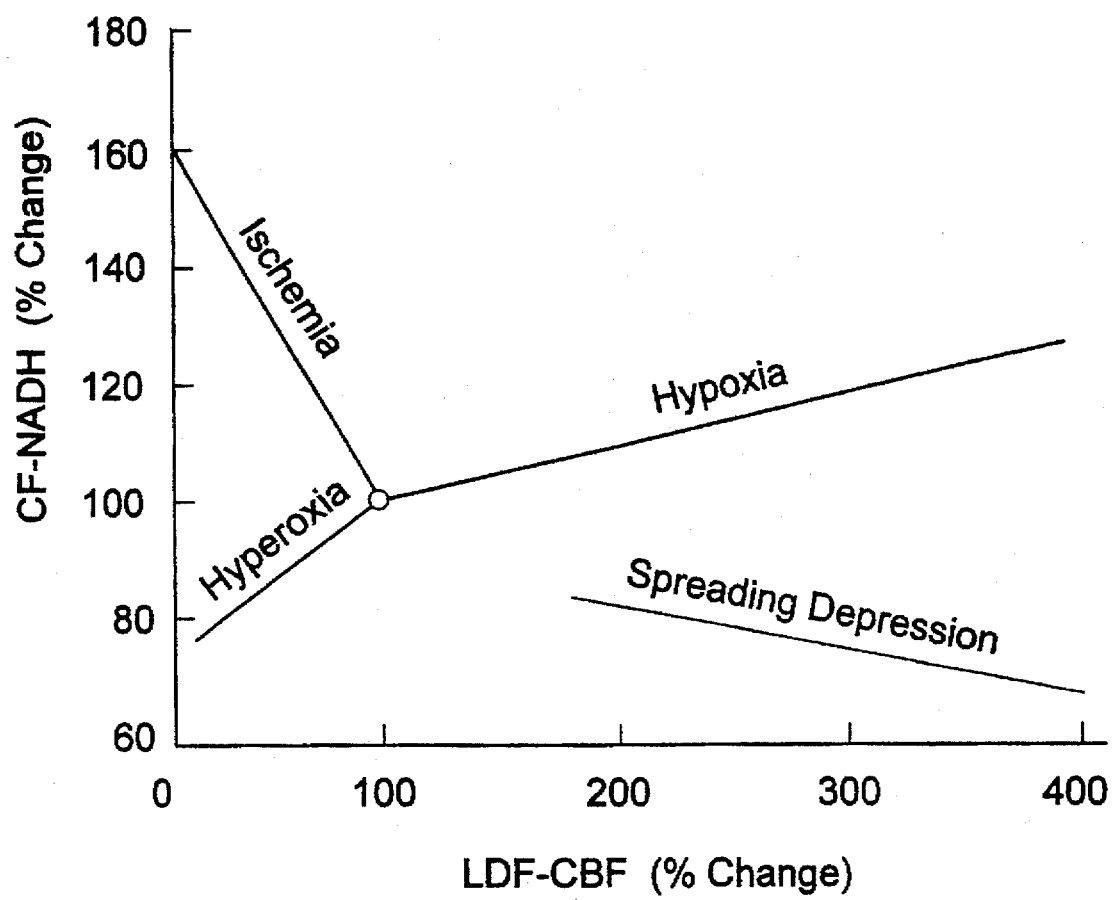
FIG. 10B is a plot of relative cerebral blood flow and NADH redox state generated using the present invention that depicts the correlation between blood flow and NADH. The lines in the figures are regression lines calculated from experimental results obtained from a group of 8 gerbils an 7 rats.

It has been found that monitor cerebral blood flow or NADH redox state alone will not provide reliable information due to various unclear responses to pathological events such as hypoxia, ischemia, hyperoxia or brain stimulation, e.g., epileptic activity or spreading depression. The minimum requirements for multiprobe assembly set forth immediately above have been validated by experiments performed upon a group of gerbils and rats exposed to graded hypoxia, ischemia, hyperoxia and spreading depression (FIG. 10B).

Example 4

Figure 9A:
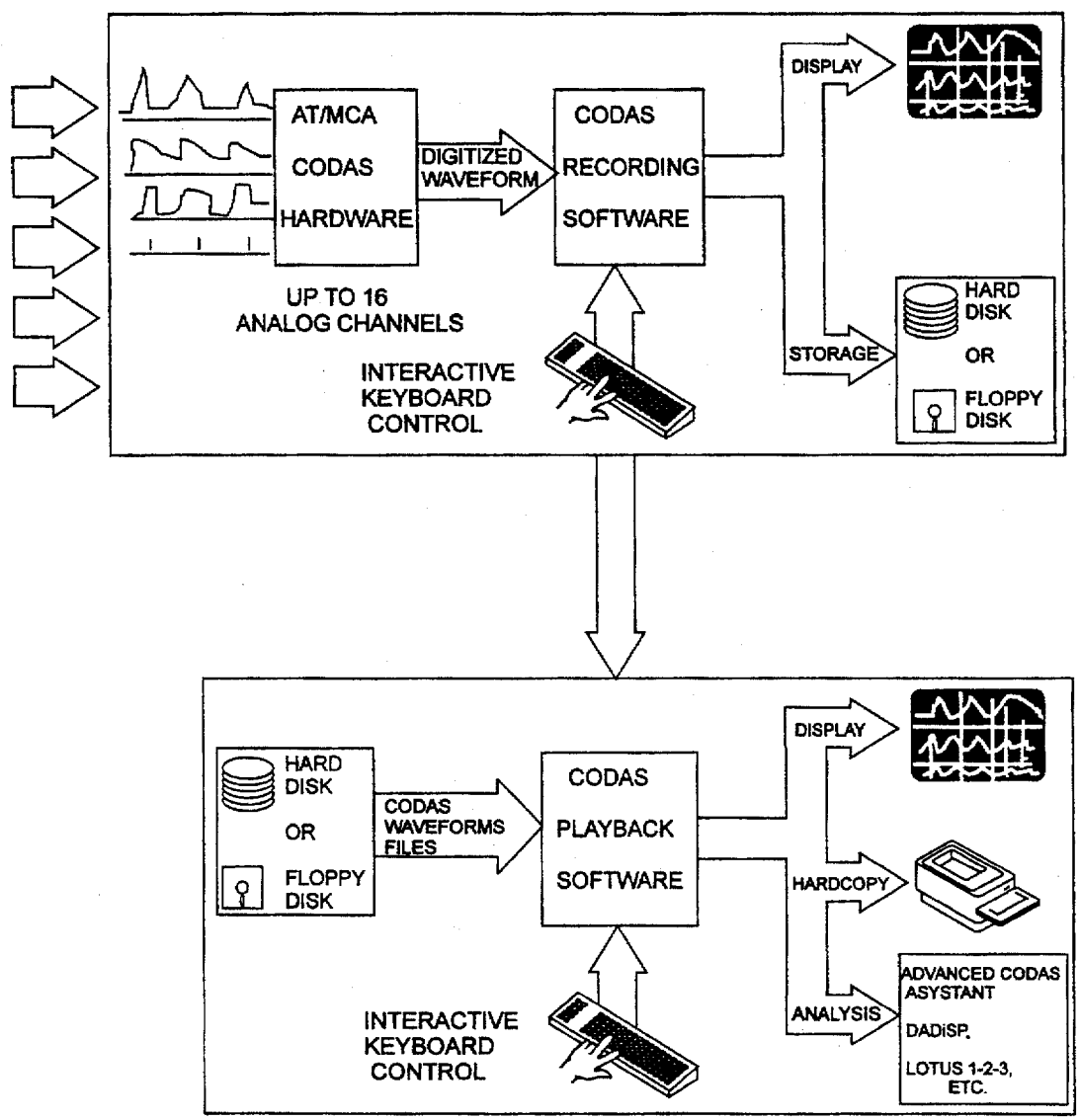
FIG. 9A is a functional block diagram of the data acquisition and signal processing system used in a preferred embodiment of the present invention.
Figure 9B:
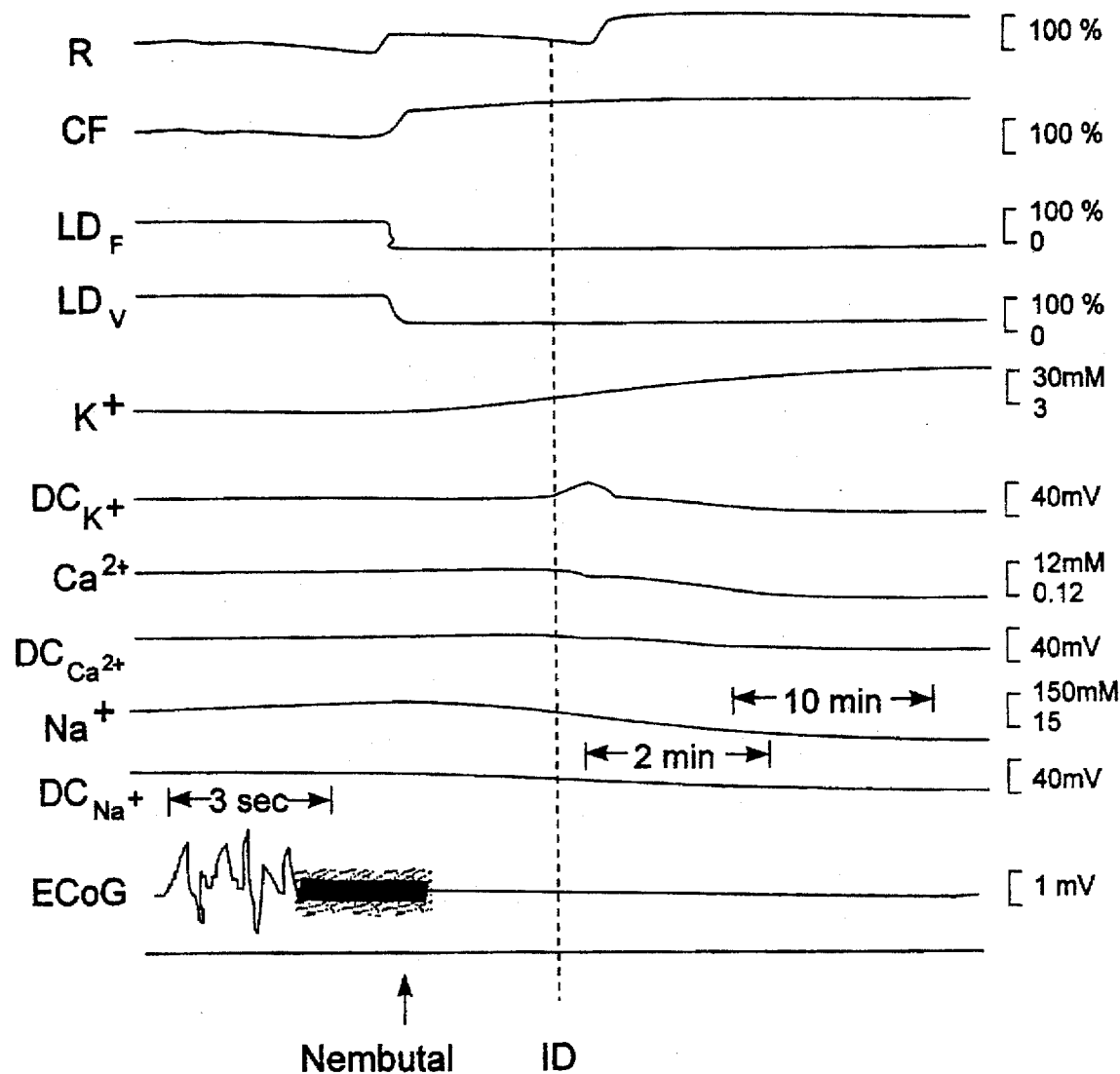
FIG. 9B. Effects of overdose injection of Nembutal (barbiturate anesthesia) on the various parameters monitored from the brain of a normal rat.

The above preferred multiprobe assembly is arranged as further shown by the functional block diagram portion of FIG. 9A. In addition to the fluorometer and the laser Doppler flowmeter discussed, an EEG amplifier monitors various brain functions a six channel electrometer monitors the ion concentration changes, and a pressure transducer monitors pressure as well as brain temperature. Data acquisition may commence immediately after the multiprobe assembly is located on the cortex. As shown in FIG. 9A, the analog signals form the laser Doppler flowmeter, EEG amplifier, fluorometer, pressure transducer and electrometer are digitized at the input of acquisition set up. The acquisition set up comprises a data processor (any 486, or comparable, processor) which includes an analog-to-digital converter which provides for up to channels (DATAQ Inc.) The data processor further includes other appropriate hardware, such as a multichannel analyzer and the hardware, necessary to input digitized waveforms into the control and data acquisition system (CODAS) recording software. A display and storage device, which may include both hard disk and/or floppy disk storage, are also provided, along with an interfacing keyboard control that is connected to the acquisition software. FIG. 9B. Shows the change in the various output signals caused by an overdose of Nembutal.

As further illustrated in FIG. 9, after the cerebral blood flow, NADH redox state, parenchymal pressure, and ion concentrations have been monitored and recorded by the acquisition set up, the data are analyzed by the analysis system. The CODAS playback software retrieves the recorded data from the storage device. The data are then analyzed by further software appropriately chosen for the required computation and the capabilities of the processors being used. The selection and use of such software is well known to those skilled in the art. An interactive keyboard control is again provided. Finally, the data, either before or after final processing, may be displayed on the display, or printed out as a hard copy report using a printer.

The most crucial test of the correlation between the intramitochondrial NADH redox state and the oxygenation of hemoglobin obtained from the Erlanger Microlight Guide Spectrophotometer (Mayevsky et al., Multiparametric evaluation of brain functions in the Mongolian gerbil in vivo. J. Basic & Clinical Physiol. & Phannacol, 3:323–342 (1992)) are in a hypoxia or oxygen lack where the inspired oxygen or the animal is reduced to the point where it can no longer maintain hemoglobin oxygenated nor NADH oxidize. This is depicted in the traces of FIG. 10A. In this figure, the abscissa is time or level of oxygen in the inspired air and the ordinate is NADH fluorescence (CF) increase upward, and oxyhemoglobin decrease (HbO$_2$) during hypoxia. The Hb trace is the total concentration of hemoglobin, which may be regarded as a blood volume signal. The animal is caused to breathe different O$_2$ levels including pure nitrogen and it is seen that there is a clear correlation between the decrease in blood oxygenation and increase in NADH redox state. Blood volume was increased as indicated by the elevated Hb signal and a decrease in the R signal (reflectance). As this trace approaches its maximum, the oxygen concentration in the tissue now reaches the critical level for the NADH response. Both traces reach maximal levels where very little if any oxygen is present in the brain tissue. Under these conditions the blood volume signals reached the highest values. However, on restoration of 100% oxygen breathing to the animal all traces abruptly respond. The NADH returns to the initial baseline prior to hypoxia, and the hemoglobin trace swings to a much more oxygenated state than prior to hypoxia, termed "hyperemia", which is caused by the blood volume flowing through the opened capillaries of the brain being greatly increased, a typical response to the restoration of oxygen in tissue following hypoxia. As appreciated by those of ordinary skill familiar with these biochemical phenomena, this correlation validates the close coupling of desaturation and resaturation of hemoglobin with reduction and oxidation of NADH.

Referring now to FIG. 10B, there is shown a graphic plot of the percent change in NADH vs. the percent change in relative cerebral blood flow under four different conditions. The data represented in FIG. 10B were derived using the multiprobe assembly shown in FIG. 8A and related processing equipment as described above. Those of ordinary skill will immediately appreciate the clear and significant correlation between relative cerebral blood flow and NADH redox state under reduced ischemia and hypoxia. In the case of ischemia, the decrease in flow, induced by occlusion of one or two carotid arteries, led to an increase in NADH. Under hypoxia, due to the autoregulation response an increase in cerebral blood flow was recorded simultaneously with the increase in NADH. See A. Mayersky and N. Zarchin, E. Yoles and B. Tannenbaum, "Oxygen supply to the brain in hypoxic and hyperoxic conditions. In: *Oxygen Transport in Red Blood Cells*, C. Nicolau, Ed., Pergamon Press, pp. 119– 132, 1986. When spreading depression was induced, the increase in energy requirement led to an activation of the mitochondrial respiration and oxidation of NADH was recorded (decrease in CF). See B. Chance and G. R. Williams, "Respiratory enzymes in oxidative phosphorylation. J. Kinetics of oxygen utilization: J. Biol. Chem, 17, 383–393, 1955; and B. Chance, P. Cohen, F. F. Jobsis and B. Schoener, "Intracellular oxidation-reduction states in vivo", Science, 137, 499–508. This increase in O$_2$ consumption led to an increase in cerebral blood flow in the range of up to 200–350% as compared to the normoxic values. See L. D. Lukayanova, J. Bures, "Changes in pO$_2$ due to spreading depression in the cortex and nuclear caudatus of the rat". Physiol. Bohemsolov. 16, 449–455, 1967 and Mayevsky, A. and Weiss, H. R., Cerebral blood flow and oxygen consumption in cortical spreading depression, J. CBF and Metabol. 11: 829–836 ( 1991 ).

If cerebral blood flow was the only parameter to be monitored, the differentiation between hypoxia and spreading depression would be impossible. The same is true for the differentiation between hypoxia and ischemia if one is monitoring the NADH redox state by itself. By monitoring the cerebral blood flow and NADH redox state together and using the appropriate algorithm it is possible to predict and describe more accurately the pathological state. However, since the outcome of any pathological state is the brain is projected in the ionic homeostatic situation monitoring of this parameter is necessary for the evaluation of functional state of the brain. Due to the large energy consumption by the Na+K⁺ ATPase any change in the energy supply will be correlated to the extracellular level of $K^+$. See A. J. Hansen, "The effects of anoxia on ion distribution in the brain". Physiol. Rev. 65, 101–148, 1985; A. Mayevsky, "Metabolic ionic and electrical responses to experimental epilepsy in the awake rat", Proc. First Intl. Cong. CBF Metabolism & Epilepsy, Baldey Moulinier, M. Ingvar, D. H., Meldmm, B. S. Eds. John Libbey pp. 263–270, 1984; and A. Mayevsky, "Level of ischemia and brain functions in the Mongolian gerbil in vivo". Brain Res., 524:1–9, 1990. Since changes in extracellular levels of $Ca^+$ and $Na^+$ are expected mainly during massive depolarization event it is not expected that it will happen during surgical situations. Therefore the monitoring of extracellular $K^+$ will represent the ionic state of the brain. Also, if massive depolarization will occur, it will be detected by the potassium level. Of course, since a critical parameter of the pathological state of the brain is its parenchymal pressure it is also necessary to monitor this parameter. The usage of an animal model is the only way by which one can develop the appropriate algorithm of the clinical situation.

While the invention has been described with respect to a limited number of embodiments, it will be appreciated that many variations, modifications and other applications of the invention may be made.

What is claimed is:

1. A single signal-single probe multiparameter analyzer apparatus for monitoring at least two parameters of a body tissue, comprising:
   (a) a single light source for transmitting a single light beam substantially of a single wavelength to a single volume element of the body tissue;
   (b) a single light receiver for receiving resultant light from the single volume element body tissue, and for conveying said received light;
   (c) a light splitter assembly connected to said single light receiver for splitting said received light into at least two split light portions;
   (d) at least two detectors, each of said detectors receiving one of said split light portions, and each of said detectors simultaneously monitoring redox state of the body tissue and microcirculatory blood flow to the body tissue portion; and
   (e) a processor connected to the at least two detectors for correlating the redox state of the tissue with the blood flow to the tissue.

2. The apparatus of claim 1, wherein said single light source is selected from the group consisting of Mercury lamp and He-Cd laser.

3. The apparatus of claim 1, wherein said single wavelength is selected from the group consisting of 366 nm and 324 nm.

4. The apparatus of claim 1, wherein said single light source includes a first bundle of optical fibers to transmit said light from said light source to the body tissue, and said single light receiver includes a second bundle of optical fibers to receive said resultant light and transmit said resultant light to said light splitter, and said first bundle and said second bundle are joined in a Y shape which transmits out said light from said light source and transmits in said resultant light to said light splitter.

5. The apparatus of claim 1, wherein one of said detectors is a fluorometer and another of said detectors is a Doppler Analyzer.

* * * * *